United States Patent [19]
Philippe et al.

[11] Patent Number: 6,093,412
[45] Date of Patent: *Jul. 25, 2000

[54] COSMETIC AND DERMATOLOGICAL COMPOSITIONS CONTAINING AMINOALCOHOL DERIVATIVES CONTAINING A UREA FUNCTIONAL GROUP AND USES THEREOF

[75] Inventors: Michel Philippe, Wissous; Christian Blaise, Saint Mande; Rémy Tuloup, Paris, all of France

[73] Assignee: L'oréal, Paris, France

[ * ] Notice: This patent is subject to a terminal disclaimer.

[21] Appl. No.: 09/357,215

[22] Filed: Jul. 20, 1999

Related U.S. Application Data

[63] Continuation of application No. 08/886,457, Jul. 1, 1997, Pat. No. 6,010,707.

[30] Foreign Application Priority Data

Jul. 1, 1996 [FR] France ................................ 96 08173

[51] Int. Cl.[7] ...................................................... A61K 7/48
[52] U.S. Cl. .......................... 424/401; 424/70.1; 424/450; 514/844; 514/845; 514/846; 514/937; 514/944
[58] Field of Search ..................... 424/401, 70.1, 424/450; 514/844, 845, 846, 937, 944

[56] References Cited

U.S. PATENT DOCUMENTS 6,010,707  1/2000  Philippe et al. ......................... 424/401

OTHER PUBLICATIONS

A.C. Williams et al., "Urea Analogues in Propylene Glycol as Penetration Enhancers in Human Skin," Int'l Jour. of Pharm., vol. 36, 1989, pp. 43–50.
NL 741311 Abstract Nov. 1, 1974.
DE 2703185 Abstract Aug. 10, 1978.
EP 0383024 Abstract Jan. 15, 1990.

*Primary Examiner*—Jyothsan Venkat
*Attorney, Agent, or Firm*—Finnegan, Henderson, Farabow, Garrett & Dunner, L.L.P.

[57] ABSTRACT

The invention relates to the use of aminoalcohol derivatives containing a urea functional group corresponding to the following formula:

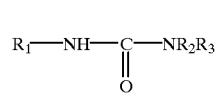

(I)

in which:

$R_1$ represents a linear or branched, saturated or unsaturated alkyl radical having from 8 to 22 carbon atoms;

$R_2$ represents a hydrogen atom or a linear or branched, saturated alkyl radical having from 1 to 6 carbon atoms;

$R_3$ represents a linear or branched, monohydroxylated or polyhydroxylated, saturated alkyl group having from 1 to 10 carbon atoms, in and for the preparation of cosmetic or dermatological compositions. These compounds are used in particular as moisturizing agents in care products for the skin or as conditioning agents in hair products.

5 Claims, No Drawings

COSMETIC AND DERMATOLOGICAL COMPOSITIONS CONTAINING AMINOALCOHOL DERIVATIVES CONTAINING A UREA FUNCTIONAL GROUP AND USES THEREOF

This is a continuation of application Ser. No. 08/886,457, filed Jul. 1, 1997 now U.S. Pat. No. 6,010,707 which is incorporated herein by reference.

The present invention relates to the use of aminoalcohol derivatives containing a urea functional group in and for the preparation of cosmetic or dermatological compositions, in particular to their use as moisturizing agents in care products for the skin or as conditioning agents in hair products.

A number of aminoalcohol compounds containing a urea functional group are known in the state of the art. Some have been described in particular in U.S. Pat. No. 3,135,790 and are used as emulsifying agents in paint or lacquer formulations or as synthetic intermediates. Others, such as those described in German Patent DE 1,125,905, in particular N-methyl-N-(2,3,4,5,6-pentahydroxy-n-hexyl)-N'-n-octylurea, are used as textile additives, washing agents or crosslinking agents or as emulsifiers. Some aminoalcohol derivatives containing a urea functional group are used in U.S. Pat. No. 2,891,944.for their insecticidal properties. A description has also been given, in the article *J. Med. Chem.*, 31(4), 858–863, 1988, for its activity with respect to certain cancerous cells, of 3-(3-octadecylureido)-1,2-propanediol.

The inventors have discovered, surprisingly, that specific aminoalcohol derivatives containing a urea functional group, the structure of which will be defined hereinbelow, exhibited advantageous cosmetic properties, in particular moisturizing products with respect to the skin.

This is because it was found that, by applying these products on the skin, it is possible to decrease the water loss thereof and/or to increase the attachment of water in the stratum corneum. These compounds can thus be used as moisturizing agents, in particular for human skin.

They make it possible to retain or to restore the flexibility of the skin, its elasticity, its resistance to the movement of the body and its function of barrier to the entry of toxic substances. They can thus be used in care products for dry skin or skin predisposed towards drying.

These compounds unexpectedly exhibit a very much greater barrier activity with respect to permeability to water on the skin than their carbamate or amide homologues known in cosmetics for their moisturizing properties.

The inventors have also discovered, surprisingly, that the aminoalcohol derivatives containing a urea functional group according to the invention, used in hair compositions, confer a particularly soft feel on hair and facilitate the disentangling thereof. They can be used as hair conditioning agents.

The main subject of the invention thus relates to the use of aminoalcohol derivatives containing a urea functional group, which will be defined subsequently, in and for the preparation of cosmetic or dermatological compositions.

Another subject of the invention relates to the cosmetic or dermatological compositions containing these aminoalcohol derivatives containing a urea functional group.

Another subject of the invention thus relates to the use of these aminoalcohol derivatives containing a urea functional group as moisturizing agents in and for the preparation of compositions for the care of the skin.

Another subject of the invention thus relates to the use of these aminoalcohol derivatives containing a urea functional group as hair conditioning agents in and for the preparation of hair compositions.

Other subjects will become apparent in the light of the description and examples which follow.

The aminoalcohol derivatives containing a urea functional group in accordance with the invention correspond to the following general formula (I):

in which:

$R_1$ represents a linear or branched, saturated or unsaturated alkyl radical having from 8 to 22 carbon atoms;

$R_2$ represents a hydrogen atom or a linear or branched, saturated alkyl radical having from 1 to 6 carbon atoms;

$R_3$ represents a linear or branched, monohydroxylated or polyhydroxylated, saturated alkyl group having from 1 to 10 carbon atoms.

$R_1$ preferably represents a linear or branched, saturated or unsaturated, $C_{10}$–$C_8$ alkyl radical.

$R_2$ preferably represents a hydrogen or the methyl group.

$R_3$ preferably represents a radical:

in which n represents an integer equal to 0 or 1, m represents an integer of between 0 and 5 and Z is a monohydroxylated or polyhydroxylated alkyl radical having from 1 to 4 carbon atoms. In particular, Z is selected from the following radicals:

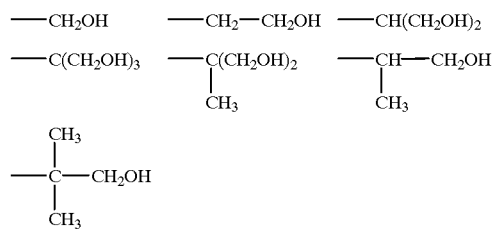

The more preferential $R_3$ radicals are selected from:

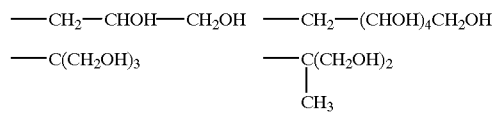

Mention may in particular be made, among the preferred compounds corresponding to the general formula (I), of:
N-dodecylaminocarbonyl-N-methyl-D-glucamine;
N-octylaminocarbonyl-N-methyl-D-glucamine;
1-dodecyl-3-(2-hydroxy-1,1-bis(hydroxymethyl)ethyl)urea;
N-dodecylaminocarbonyl-D-glucamine;
1-(2,3-dihydroxypropyl)-3-dodecylurea;
1-dodecyl-3-(2-hydroxy-1-hydroxymethyl-1-methylethyl) urea;
1-(2-ethylhexyl)-3-(2-hydroxy-1,1-bis(hydroxymethyl) ethyl)urea;
N-(4Z)-octadec-9-enylaminocarbonyl-N-methyl-D-glucamine.

These compounds can be obtained by reaction, in a preferably polar solvent, of an aminoalcohol of formula $R_2$—NH—$R_3$, in which $R_2$ and $R_3$ have the same meanings as those indicated above, with an imidazoloalkylcarboxamide compound of formula (III):

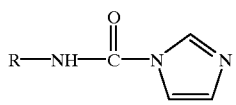

(III)

The reaction is generally carried out in an inert atmosphere in the presence of a solvent such as methanol, at the temperature corresponding to reflux of the solvent, preferably between 40 and 50° C.

The imidazoloalkylcarboxamide compounds of formula (II) are obtained according to known synthetic methods, in particular known in the following reference: *Angewandte Chemie*, International Edition, Vol. 1, No. 7, 1962 the disclosure of which is incorporated herein by reference.

The cosmetic or dermatological compositions according to the invention are characterized in that they contain, in a cosmetically or dermatologically acceptable vehicle, at least one compound of formula (I) as defined above, with the exception of the compound N-methyl-N-(2,3,4,5,6-pentahydroxy-n-hexyl)-N'-n-octylurea.

The cosmetic or dermatological compositions according to the invention preferably comprise 0.001 to 15% by weight of compound of formula (I) with respect to the total weight of the composition.

The cosmetically acceptable vehicle used in the compositions of the invention is selected from water; organic solvents compatible with a cutaneous or hair application such as acetone, isopropanol or ethanol; triglycerides of fatty acids containing 6–24 carbon atoms, glycol ethers, polyalkylene glycol esters and volatile silicones or their mixtures.

The compositions can be provided in the form of a single-phase or multi-phase aqueous or aqueous/alcoholic lotion, of a single-phase or multi-phase gel, of an emulsion, of a cream, of a vesicular dispersion of ionic or non-ionic lipids, it being possible for the said vesicles then to act as encapsulation agent for lipophilic or hydrophilic active ingredients, of a foam or of a spray.

The compositions for the care of the skin according to the invention can be provided in the form of a lotion, gel, emulsion, cream or foam to be applied on the skin.

The hair compositions can be provided in the form of a shampoo, of a conditioner of the rinse-out or leave-in type, of perming, hair-straightening, dyeing or bleaching compositions or alternatively in the form of rinse-out compositions, to be applied before or after dyeing, perming or hair-straightening or alternatively between the two stages of a perming operation or of a hair-straightening operation.

The cosmetic or dermatological compositions can, moreover, contain conventional cosmetic additives chosen from fatty substances, organic solvents, silicones, thickeners, softeners, surfactants, anionic, cationic, non-ionic or amphoteric polymers, antifoaming agents, hair conditioning agents, such as proteins, vitamins, treating agents (agents for combatting hair loss, antidandruff agents), dyes, fragrances, preservatives or propellants.

Use may more specifically be made, as fatty substance, of an oil or wax or their mixture, fatty acids, fatty alcohols, fatty acid esters, such as $C_6$–$C_{18}$ fatty acid triglycerides, petrolatum, paraffin, lanolin or hydrogenated or acetylated lanolin.

Mention may be made, among the oils, of mineral, animal or vegetable oils or synthetic oils and in particular liquid petrolatum, liquid paraffin, castor oil, jojoba oil or sesame oil, as well as silicone oils and gums and isoparaffins.

Mention may be made, among the waxes, of animal, vegetable, mineral or synthetic waxes and in particular beeswax, candelilla wax, ozokerites or microcrystalline waxes, as well as silicone waxes and resins.

Mention may more specifically be made, among the organic solvents conventionally used in cosmetic compositions, of lower $C_1$ to $C_6$ monoalcohols or polyalcohols, such as ethanol, isopropanol, ethylene glycol, diethylene glycol, propylene glycol or glycerol.

The thickening agents can be selected from sodium alginate, gum arabic, cellulose derivatives, such as methyl cellulose, hydroxymethyl cellulose, hydroxyethyl cellulose, hydroxypropyl cellulose or hydroxypropylmethyl cellulose, guar gum or its derivatives, xanthan gum, scleroglucans or crosslinked polyacrylic acids.

Use may be made, as surface-active agents and as polymers, of all those well known in the state of the art, in particular for their use in hair compositions.

The compositions can be provided in the form of a vesicular dispersion of ionic or non-ionic amphiphilic lipids. They are prepared in particular by causing the lipids to swell in an aqueous solution in order to form spherules dispersed in the aqueous medium, as described in Standish & Watkins, J. Mol. Biol., 13, 238 (1965) or in French Patents FR-A-2, 315,991 and FR-A-2,416,008 the disclosures of which are incorporated herein by reference. The various types of preparation processes are described in "Les liposomes en biologie cellulaire et pharmacologie" [Liposomes in Cell Biology and Pharmacology], published by INSERM/John Libery Eurotext, 1987, pages 6 to 18, the disclosure of which is incorporated herein by reference.

The pH of the compositions according to the invention is generally between 4 and 8 and preferably between 5 and 7.

A number of examples of the preparation of compounds according to the invention, as well as examples of cosmetic compositions containing them, will now be given by way of illustration and without any limiting nature.

EXAMPLE 1

Synthesis of N-dodecylaminocarbonyl-N-methyl-D-glucamine

First stage: Synthesis of 1-N-(dodecylaminocarbonyl) imidazole of formula (III) ($R_1$=$C_{12}H_{25}$)

49 g of N,N'-carbonyldiimidazole were dissolved in 700 cm³ of anhydrous dimethylformamide in a reactor and the solution was maintained under an inert atmosphere. 55 g of laurylamine were added, in such a way as to maintain the temperature at a value of less than 30° C. The mixture was kept stirring at room temperature for 8 hours. The resulting reaction mixture was poured into 2 litres of water and the precipitate obtained was filtered off.

After drying, 75 g (90% yield) of 1-N-(dodecylaminocarbonyl)imidazole were obtained in the form of a white powder.

Second stage: Synthesis of N-dodecylaminocarbonyl-N-methyl-D-glucamine of formula (I) ($R_1$=$C_{12}H_{25}$, $R_2$=$CH_3$, $R_3$=—$CH_2$—$(CHOH)_4$—$CH_2OH$)

42 g of 1-N-(dodecylaminocarbonyl)imidazole and 32 g of N-methyl-D-glucamine were suspended, under an inert atmosphere, in 400 cm³ of methanol. The reaction mixture was kept stirring at reflux for 4 hours. The reaction mixture was cooled with an ice bath and the precipitate was then filtered off. It was washed with 500 cm³ of water and then dried. 49 g (80% yield) of N-dodecylaminocarbonyl-N-methyl-D-glucamine were obtained in the form of a white powder.

Elemental analysis

|  | C | H | N | O |
|---|---|---|---|---|
| Calculated (%) | 59.09 | 10.41 | 6.89 | 23.61 |
| Found (%) | 58.83 | 10.45 | 6.96 | 23.37 |

200 MHz $^1$H NMR spectrum conforms
Melting point: 116.8° C. (FP 89)

EXAMPLE 2

Synthesis of 1-dodecyl-3-(2-hydroxy-1,1-bis(hydroxymethyl)ethyl)urea of formula (I)

($R_1$=$C_{12}H_{25}$, $R_2$=H, $R_3$=—C—$(CH_2OH)_3$)

The preparation was carried out, according to the same process described in Example 1, from 5.2 g of trihydroxymethylaminomethane of corresponding formula $R_2$—NH—$R_3$, where $R_2$ denoted H and $R_3$ denoted —C—$(CH_2OH)_3$, and 8 g of 1-N-(dodecylaminocarbonyl)imidazole of corresponding formula (II), where $R_1$ denoted $C_{12}H_{25}$, in 100 cm$^3$ of methanol.

Elemental analysis

|  | C | H | N | O |
|---|---|---|---|---|
| Calculated (%) | 61.41 | 10.91 | 8.43 | 19.25 |
| Found (%) | 61.40 | 11.08 | 8.29 | 19.12 |

200 MHz $^1$H NMR spectrum conforms
Melting point: 132.4° C. (FP 89)

EXAMPLE 3

Synthesis of N-dodecylaminocarbonyl-D-glucamine of formula (I) ($R_1$=$C_{12}H_{25}$, $R_2$=H, $R_3$=—$CH_2$—$(CHOH)_4$—$CH_2OH$)

The preparation was carried out according to the same process described in Example 1, from 6.1 g of D-glucamine of corresponding formula $R_2$—NH—$R_3$, where $R_2$ denoted H and $R_3$ denoted —$CH_2$—$(CHOH)_4$—$CH_2OH$, and 7 g of 1-N-(dodecylaminocarbonyl)imidazole of corresponding formula (II), where $R_1$ denoted $C_{12}H_{25}$, in 100 cm$^3$ of methanol.

Elemental analysis

|  | C | H | N | O |
|---|---|---|---|---|
| Calculated (%) | 58.14 | 10.27 | 7.14 | 24.46 |
| Found (%) | 58.09 | 10.21 | 7.18 | 24.73 |

200 MHz $^1$H NMR spectrum conforms
Melting point: 161.5° C. (FP 89)

EXAMPLE 4

Synthesis of 1-(2,3-dihydroxypropyl)-3-dodecylurea of formula (I) ($R_1$=$C_{12}H_{25}$, $R_2$=H, $R_3$=—$CH_2$—CHOH—$CH_2OH$)

The preparation was carried out according to the same process described in Example 1, from 2.3 g of 3-amino-1,2-propanediol of corresponding formula $R_2$—NH—$R_3$, where $R_2$ denoted H and $R_3$ denoted —$CH_2$—CHOH—$CH_2OH$, and 7 g of 1-N-(dodecylaminocarbonyl)imidazole of corresponding formula (II), where $R_1$ denoted $C_{12}H_{25}$, in 100 cm$^3$ of methanol.

Elemental analysis

|  | C | H | N | O |
|---|---|---|---|---|
| Calculated (%) | 63.54 | 11.33 | 9.26 | 15.87 |
| Found (%) | 63.51 | 11.45 | 9.14 | 16.09 |

200 MHz $^1$H NMR spectrum conforms
Melting point: 121.5° C. (FP 89)

EXAMPLE 5

Synthesis of 1-dodecyl-3-(2-hydroxy-1-hydroxymethyl-1-methylethyl)urea of formula (I)

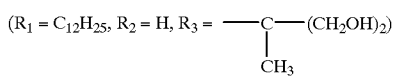

The preparation was carried out, according to the same process described in Example 1, from 3.5 g of 2-amino-2-methyl-1,3-propanediol of corresponding formula $R_2$—NH—$R_3$, where $R_2$ denoted H and $R_3$ denoted:

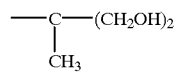

and 7 g of 1-N-(dodecylaminocarbonyl)imidazole of corresponding formula (III), where $R_1$ denoted $C_{12}H_{25}$, in 100 cm$^3$ of methanol.

Elemental analysis

|  | C | H | N | O |
|---|---|---|---|---|
| Calculated (%) | 64.52 | 11.47 | 8.85 | 15.17 |
| Found (%) | 64.52 | 11.43 | 8.84 | 15.00 |

200 MHz $^1$H NMR spectrum conforms
Melting point: 60.1° C. (FP 89)

EXAMPLE 6

Synthesis of 1-(2ethylhexyl)-3-(2-hydroxy-1,1-bis(hydroxymethyl)ethyl)urea of formula (I)

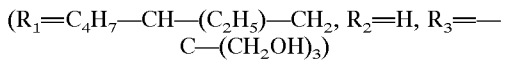

The preparation was carried out, according to the same process described in Example 1, from 14 g of trihydroxymethylaminomethane of corresponding formula $R_2$—NH—$R_3$, where $R_2$ denoted H and $R_3$ denoted —C—$(CH_2OH)_3$, and 25 g of 1-N-(2-ethylhexylaminocarbonyl)imidazole of corresponding formula (III), where $R_1$ denoted $C_4H_7$—CH—$(C_2H_5)$—$CH_2$, in 200 cm$^3$ of methanol.

Elemental analysis

|  | C | H | N | O |
|---|---|---|---|---|
| Calculated (%) | 56.50 | 10.21 | 10.14 | 23.16 |
| Found (%) | 56.56 | 10.35 | 10.23 | 23.38 |

200 MHz $^1$H NMR spectrum conforms
Melting point: 155.8° C. (FP 89)

EXAMPLE 7

Synthesis of N-(4Z)-octadec-9enylaminocarbonyl-N-methyl-D-glucamine of formula (I) ($R_1$=$C_8H_{17}$—CH=CH—$C_8H_{16}$, $R_2$=$CH_3$, $R_3$=—$CH_2$—$(CHOH)_4$—$CH_2OH$)

The preparation was carried out, according to the same process described in Example 1, from N-methyl-D-glucamine of corresponding formula $R_2$—NH—$R_3$, where $R_2$ denoted $CH_3$ and $R_3$ denoted —$CH_2$—$(CHOH)_4CH_2OH$, and 48 g of 1-N-(octadec-9-enylaminocarbonyl)imidazole of corresponding formula (III), where $R_1$ denoted $C_8H_{17}$—CH=CH—$C_8H_{16}$, in 300 cm$^3$ of methanol.

Elemental analysis

|  | C | H | N | O |
|---|---|---|---|---|
| Calculated (%) | 63.90 | 10.72 | 5.73 | 19.64 |
| Found (%) | 64.07 | 10.75 | 5.85 | 19.90 |

200 MHz $^1$H NMR spectrum conforms
Melting point: 116.2° C. (FP 89)

EXAMPLE 8

Synthesis of N-octylaminocarbonyl-N-methyl-D-glucamine of formula (I) ($R_1$=$C_8H_{17}$, $R_2$=$CH_3$, $R_3$=—$CH_2$—$(CHOH)_4$—$CH_2OH$)

Synthesis of 1-N-(octylaminocarbonyl)imidazole 80 g of N,N'-carbonyldiimidazole were dissolved in 900 cm$^3$ of anhydrous dimethylformamide and the solution was maintained under an inert atmosphere. 63 g of octylamine were added while maintaining the temperature below 30° C. The mixture was kept stirring at room temperature for 4 hours. The mixture was then poured into 3 litres of water in order for extraction to be carried out with 4 times 400 cm$^3$ of ethyl acetate. The combined organic extracts were dried and filtered and the filtrate was evaporated until 84 g of product were obtained in the form of a pasty oil (Yield: 86%). The 200 MHz $^1$H NMR spectrum conforms.

Synthesis of N-octyiaminocarbonyl-N-methyl-D-glucamine 47 g of 1-N-(octylaminocarbonyl)imidazole and 42 g of N-methyl-D-glucamine were suspended in 300 cm$^3$ of methanol under an inert atmosphere. The reaction mixture was maintained at reflux with stirring for 3 hours. Cooling was carried out with an ice bath and then the precipitate is filtered off. It was recrystallized from 300 cm$^3$ of ethanol. 40 g (55% yield) of N-octylaminocarbonyl-N-methyl-D-glucamine were obtained in the form of a white powder.
200 MHz $^1$H NMR spectrum conforms Mass spectrum conforms
Melting point: 111.4° C. (FP 89)

Elemental analysis

|  | C | H | N | O |
|---|---|---|---|---|
| Calculated (%) | 54.84 | 9.78 | 7.99 | 27.39 |
| Found (%) | 53.58 | 9.71 | 8.25 | 28.34 |

EXAMPLE 9

Comparative example

Measurement of the imperceptible water loss (IWL)

This measurement was carried out using an evaporimeter (Servomed) which quantitatively determines the evaporation of water, that is transportation of water by diffusion, from a stratum corneum sample which seals a cylindrical capsule containing water, the whole assembly being placed in a chamber with controlled relative temperature and controlled relative humidity.

Sensors made it possible to measure the partial vapour pressure of water at two points situated at different distances from the sample.

The partial vapour pressure of water gradient between the two points was thus determined and therefore the degree of evaporation in accordance with Fick's law.

This measurement is carried out for:

a) N-dodecylaminocarbonyl-N-methyl-D-glucamine (compound of Example 1);

b) N-dodecanoyl-N-methyl-D-glucamine, amide homologue of the compound of Example 1, known to be a moisturizing agent, which will be called Reference A;

c) N-dodecyloxycarbonyl-N-methyl-D-glucamine, carbamate homologue of the compound of Example 1, known to be a moisturizing agent, which will be called Reference B.

The compounds were prepared in the proportion of 1% in a dichloromethane/methanol (2/1 v/v) mixture and then applied on pieces of delipidated stratum corneum.

The imperceptible water loss (IWL) for each compound was measured 20 hours after application.

The following results are obtained:

| Compound | Example 1 | Reference A | Reference B |
|---|---|---|---|
| I.W.L. | −21 +/− 2 | −11 +/− 3 | −9 +/− 2 |

It was thus found that the application of the compound according to the invention makes it possible to reduce the evaporation of the water contained in the stratum corneum to a greater extent, in comparison with its amide and carbamate homologues.

EXAMPLE 10

Conditioning cream

The following composition was prepared:

| | | |
|---|---|---|
| N-Dodecylaminocarbonyl-N-methyl-D-glucamine | 2 | g AM |
| Distearyldimethylammonium chloride | 2 | g |
| Hydroxyethyl cellulose, sold under the name of Natrosol 250 HHR by Aqualon | 1 | g |
| Preservative, fragrance, dye | q.s. | |
| Water | q.s. for 100 | g |
| pH adjusted to 6 with NaOH | | |

A milky fluid cream was obtained which, after application, conferred a soft feel on the hair and made it easy to disentangle.

EXAMPLE 11

Day cream for the face

The following composition was prepared:

| The following composition was prepared | |
|---|---|
| cetyl alcohol | 2.5% |
| sorbitan tristearate | 0.9% |
| poly(ethylene oxide) stearate (polyoxyethylenated 40 times) | 2% |
| glyceryl stearate | 3% |
| myristyl myristate | 2% |
| hydrogenated polyisobutene | 2.5% |
| octyl palmitate | 4% |
| polydimethylsiloxane (10 cm².s) | 5% |
| apricot kernel oil | 5.715% |
| N-dodecylaminocarbonyl-N-methyl-D-glucamine | 0.5% |
| preservatives | 0.5% |
| water | q.s. for 100% |

A day cream was obtained which was provided in the form of an emulsion which made it possible thoroughly to cover and to protect the skin and which was particularly suitable for normal skin and dry skin.

EXAMPLE 12

Night cream

The following formulation was prepared:

| The following formulation was prepared | |
|---|---|
| mixture of glyceryl mono- and distearate and of poly(ethylene oxide) stearate | 2% |
| N-dodecylaminocarbonyl-N-methyl-D-glucamine | 3% |
| apricot kernel oil | 17% |
| cyclopentadimethylsiloxane | 1.5% |
| carbomer (sold under the trade name Carbopol) | 0.75% |
| preservatives | 0.5% |
| triethanolamine | 0.75% |
| water | q.s. for 100% |

A night cream was obtained, which was provided in the form of a thick and glossy emulsion which was very soft to apply, which proved to be nourishing and moisturizing for the skin, particularly for dry skin.

What is claimed is:

1. A method for moisturizing the skin, comprising applying to the skin an amount of a composition effective to moisturize the skin, wherein said composition comprises, in a cosmetically or dermatologically acceptable vehicle, a moisturizing agent comprising at least one aminoalcohol derivative containing a urea functional group of the following formula (I):

in which:

$R_1$ represents a linear or branched, saturated or unsaturated alkyl radical having from 8 to 22 carbon atoms;

$R_2$ represents a hydrogen atom or a linear or branched, saturated alkyl radical having from 1 to 6 carbon atoms;

$R_3$ represents a linear or branched, monohydroxylated or polyhydroxylated, saturated alkyl group having from 1 to 10 carbon atoms.

2. A method according to claim 1, wherein, in the formula (I), $R_1$ represents a saturated or unsaturated, linear or branched, $C_{10}$–$C_{18}$ alkyl radical, $R_2$ represents a hydrogen or the methyl group and $R_3$ represents a radical:

—$(CH_{2})_n$—$(CHOH)_m$—Z in which n represents an integer equal to 0 or 1, m represents an integer of between 0 and 5 and Z is a monohydroxylated or polyhydroxylated alkyl radical having from 1 to 4 carbon atoms.

3. A method according to claim 2, wherein Z is:

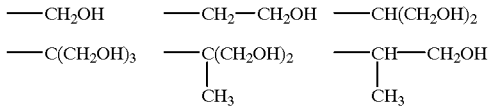

or

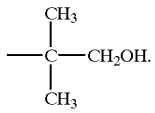

4. A method according to claim 2, wherein the $R_3$ radical is:

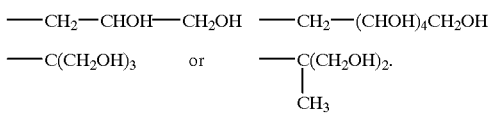

5. A method according to claim 1, wherein the compound corresponding to the general formula (I) is:
N-dodecylaminocarbonyl-N-methyl-D-glucamine;
N-octylaminocarbonyl-N-methyl-D-glucamine;
1-dodecyl-3-(2-hydroxy-1,1-bis(hydroxymethyl)ethyl)urea;
N-dodecylaminocarbonyl-D-glucamine;
1-(2,3-dihydroxypropyl)-3-dodecylurea;
1-dodecyl-3-(2-hydroxy-1-hydroxymethyl-1-methylethyl) urea;
1-(2-ethylhexyl)-3-(2-hydroxy-1,1-bis(hydroxymethyl) ethyl)urea; or
N-(4Z)-octadec-9-enylaminocarbonyl-N-methyl-D-glucamine.

* * * * *

UNITED STATES PATENT AND TRADEMARK OFFICE
CERTIFICATE OF CORRECTION

PATENT NO.: 6,093,412
DATED: July 25, 2000
INVENTOR(S): PHILIPPE et al.

It is certified that an error appears in the above-identified patent and that said Letters Patent is hereby corrected as shown below:

In claim 2, column 10, line 25, "-$(CH_{hd\ 2})_n$-$(CHOH)_m$-Z" should read --$(CH_2)_n$-$(CHOH)_m$-Z--.

Title page, item [73], "Assignee: L'oréal" should read --Assignee: L'Oréal--.

Signed and Sealed this

Seventeenth Day of April, 2001

Attest:

NICHOLAS P. GODICI

Attesting Officer     Acting Director of the United States Patent and Trademark Office